(12) United States Patent
Ganske

(10) Patent No.: US 11,554,249 B2
(45) Date of Patent: Jan. 17, 2023

(54) CATHETER STRAIN RELIEF ASSEMBLY

(71) Applicant: Surmodics, Inc., Eden Prairie, MN (US)

(72) Inventor: Karl V. Ganske, Hopkins, MN (US)

(73) Assignee: Surmodics, Inc., Eden Prairie, MN (US)

( * ) Notice: Subject to any disclaimer, the term of this patent is extended or adjusted under 35 U.S.C. 154(b) by 251 days.

(21) Appl. No.: 16/413,205

(22) Filed: May 15, 2019

(65) Prior Publication Data

US 2020/0360657 A1    Nov. 19, 2020

(51) Int. Cl.
*A61M 25/00* (2006.01)

(52) U.S. Cl.
CPC .... *A61M 25/0097* (2013.01); *A61M 25/0054* (2013.01); *A61M 25/0014* (2013.01); *A61M 25/0051* (2013.01); *A61M 25/0052* (2013.01); *A61M 2025/0059* (2013.01)

(58) Field of Classification Search
CPC .......... A61M 25/0097; A61M 25/0054; A61M 25/0052; A61M 25/0051; A61M 2025/0059; A61M 25/0014; A61M 25/0098; A61M 39/10; A61M 2025/0098
See application file for complete search history.

(56) References Cited

U.S. PATENT DOCUMENTS

| | | |
|---|---|---|
| 3,028,283 A | 4/1962 | Lundgren et al. |
| D283,840 S | 5/1986 | Matsutani |
| 4,934,934 A | 6/1990 | Arpaio, Jr. et al. |
| D332,903 S | 2/1993 | Adams |
| D363,963 S | 11/1995 | Boone et al. |
| D383,822 S | 9/1997 | Boone et al. |
| D395,068 S | 6/1998 | George |
| 5,951,494 A | 9/1999 | Wang et al. |

(Continued)

FOREIGN PATENT DOCUMENTS

| | | | |
|---|---|---|---|
| EM | 003865179-0001 | 7/2017 | |
| EP | 0937480 A1 * | 8/1999 | ........ A61M 25/0014 |
| WO | WO-2012158152 A1 * | 11/2012 | ............. A61B 50/30 |

OTHER PUBLICATIONS

"U.S. Appl. No. 29/581,755, Non Final Office Action dated Nov. 16, 2017", 7 pgs.

(Continued)

*Primary Examiner* — Nathan R Price
*Assistant Examiner* — Melissa A Snyder
(74) *Attorney, Agent, or Firm* — Schwegman Lundberg & Woessner, P.A.

(57) ABSTRACT

A catheter assembly includes a catheter shaft having shaft proximal and distal portions. A hub is coupled with the catheter shaft proximate the shaft proximal portion. A graduated strain relief fitting is coupled between the catheter shaft and the hub. The graduated strain relief fitting includes at least a first flexural modulus proximate the hub and a fitting proximal portion. The graduated strain relief fitting includes a second flexural modulus proximate the catheter shaft and a fitting distal portion. The second flexural modulus is less than the first flexural modulus and less than or equal to a catheter shaft flexural modulus. The first and second flexural moduli are modulated with one or more of a taper, flexure joints, fitting frame of the fitting or material of the fitting body.

22 Claims, 6 Drawing Sheets

(56) References Cited

U.S. PATENT DOCUMENTS

| | | | |
|---|---|---|---|
| 6,228,073 B1* | 5/2001 | Noone | A61M 25/0014 |
| | | | 128/912 |
| 6,245,053 B1 | 6/2001 | Benjamin | |
| D469,137 S | 1/2003 | Huang | |
| D532,472 S | 11/2006 | Schauffele et al. | |
| 7,708,704 B2* | 5/2010 | Mitelberg | A61M 25/0043 |
| | | | 604/528 |
| 7,780,611 B2 | 8/2010 | Griego et al. | |
| D647,990 S | 11/2011 | Symonds | |
| D662,810 S | 7/2012 | Clarke | |
| D735,825 S | 8/2015 | Lamkin et al. | |
| D750,246 S | 2/2016 | Scianamblo | |
| D760,386 S | 6/2016 | Watanabe | |
| 9,486,678 B2 | 11/2016 | Lamkin et al. | |
| D817,894 S | 5/2018 | Ganske | |
| 2001/0049519 A1* | 12/2001 | Holman | B29C 45/14598 |
| | | | 604/534 |
| 2006/0264904 A1* | 11/2006 | Kerby | A61M 25/0021 |
| | | | 604/523 |
| 2010/0057037 A1* | 3/2010 | Webler | A61M 25/0052 |
| | | | 604/500 |

OTHER PUBLICATIONS

"U.S. Appl. No. 29/581,755, Notice of Allowance dated Mar. 14, 2018", 7 pgs.
"U.S. Appl. No. 29/581,755, Response filed Jan. 15, 2018 to Non Final Office Action dated Nov. 16, 2017", 6 pgs.
"ASAHI Caravel, ASAHI Corsair Pro Microcatheter, Tornus Product Pages", ASAHI INTECC Co., Ltd., (2016), 4 pgs.
"Pronto V4 Extraction Catheter Product Pages", Vascular Solutions, Inc., (2016), 3 pgs.

* cited by examiner

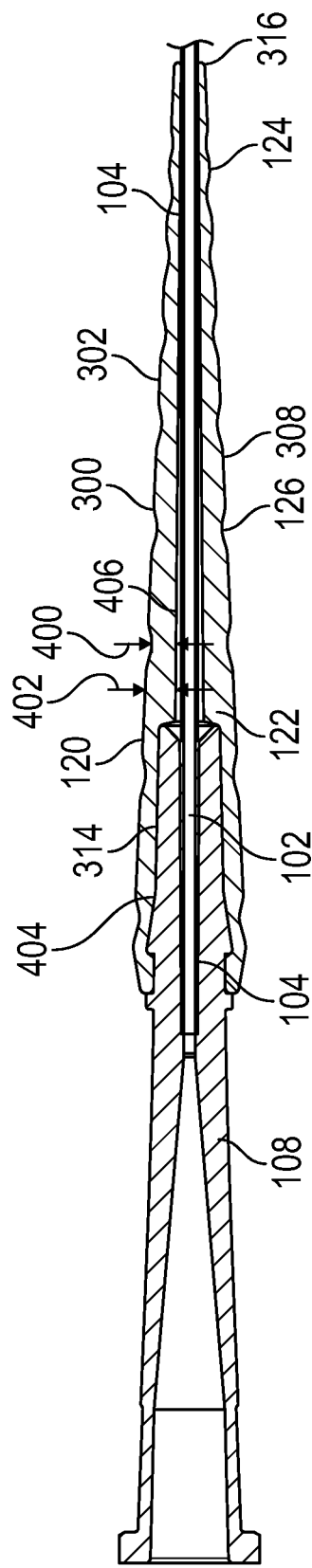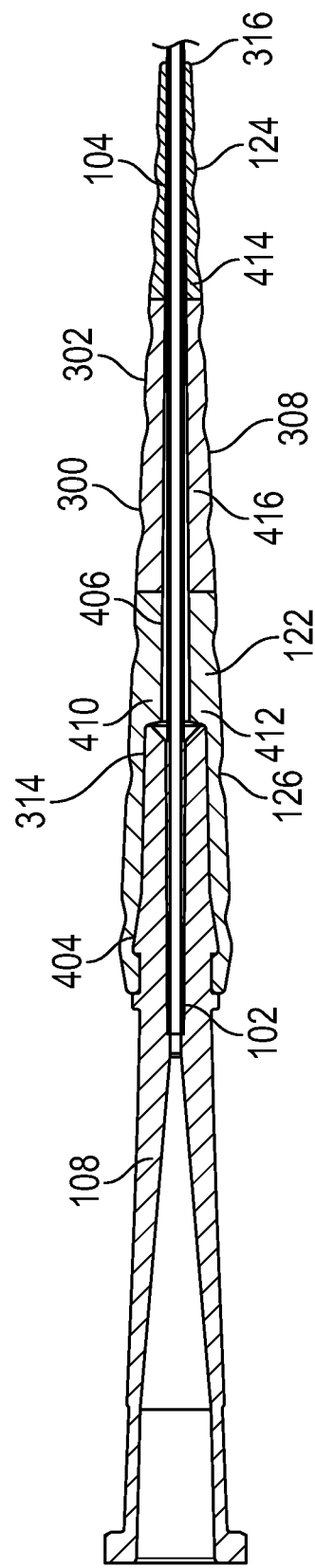
FIG. 4A
FIG. 4B

CATHETER STRAIN RELIEF ASSEMBLY

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright SurModics, Inc. of Eden Prairie, Minn. All Rights Reserved.

TECHNICAL FIELD

This document pertains generally, but not by way of limitation, to deflectable medical devices including catheters.

BACKGROUND

Elongate medical instruments configured for operation include shafts, such as catheter shafts connected with a hub or handle. The hub is manipulated by the medical profession to correspondingly manipulate the catheter shaft, for instance within a patient. In some examples, the hub has an enlarged profile relative to the profile of the catheter shaft to facilitate manipulation. For instance, the hub is an elongate structure that is wider than the catheter shaft. A proximal portion of the catheter shaft is fit within the hub to interconnect the components.

The medical professional manipulates the hub and thereby manipulates the catheter shaft. In some examples, manipulation includes longitudinal movement of the catheter shaft (e.g., along its longitudinal axis) through vasculature, cavities or the like. In other examples, the hub is rotated, moved laterally or the like to correspondingly rotate the catheter shaft or deflect the catheter shaft (e.g., into a curved or bowed configuration) to navigate the catheter shaft through bends, turns and corners within vasculature or cavities.

SUMMARY

The present inventors have recognized, among other things, that a problem to be solved includes minimizing kinking-related damage to elongate medical devices, such as catheters, and corresponding risk to patients. As previously described medical devices, such as catheters, include an elongate catheter shaft having a smaller profile than a hub connected with the shaft. In some examples, a proximal end of the catheter shaft is received within the hub and fixed to the hub (e.g., with adhesives, welds, interference fitting or the like). A clinician manipulates the catheter shaft longitudinally, rotationally and laterally to orient the catheter shaft as desired. In some examples, the hub and catheter shaft are rotated, moved laterally or the like to navigate vasculature or traverse a cavity.

The catheter shaft is deflected during manipulation into one or more curved configurations. In some examples, the curved configurations facilitate navigation through vasculature, such as tortuous vasculature. For instance, the clinician provides torque or lateral force to the hub, and the catheter shaft rotates and deflects accordingly. The small profile of the catheter shaft relative to the hub facilitates the deflection of the catheter shaft, and one or more of materials, construction techniques or the like resist failure of the catheter shaft, for instance by kinking (e.g., including deformation through kinking, buckling, fracture or the like).

Stress risers along the catheter shaft increase the risk of kinking. For instance, the profile change at the coupling between the hub and the catheter shaft provides a sharp hub interface between the shaft and the hub and a corresponding stress riser. Deflection of the catheter shaft during manipulation generates enhanced stresses at the sharp interface and corresponding kinking. Some example catheter assemblies include strain relief fittings that support the proximal end of the catheter shaft (e.g., projecting distally from the hub) to minimize kinking at the hub and shaft interface. In some of these examples, the strain relief fitting provides another stress riser at the fitting interface between the catheter shaft and a distal end of the strain relief fitting. The strain relief fitting includes materials that provide increased structural integrity (e.g., have an increased flexural modulus relative to the catheter shaft). The relatively rigid strain relief fitting (compared to the catheter shaft) provides another stress riser at the fitting interface distal to the proximal stress riser the strain relief fitting addresses at the hub interface.

The present subject matter provides a solution to this problem, for instance with a catheter assembly including a graduated strain relief fitting. The graduated strain relief fitting is coupled between a hub and a catheter shaft, for instance proximate to the hub interface. The fitting includes a polymer (e.g., a thermoplastic such as Santoprene or the like) that provides support to the catheter shaft and accordingly minimizes kinking at the hub interface.

The graduated strain relief fitting includes one or more of a profile, profile changes, material variations, or the like that control the flexural modulus of the fitting between the fitting proximal and distal ends. In one example, the graduated strain relief fitting includes a tapered profile that decreases from the proximal end to the distal end. In another example, the graduated strain relief fitting includes one or more scalloped flexure joints (e.g., channel, groove, flute, helix, notch, recess, dimple, scoring or the like) that selectively decrease wall thickness of the fitting and accordingly control the flexural modulus. In still other examples, the material of the graduated strain relief fitting is varied between the proximal and distal ends, for instance to profile a first higher flexural modulus proximate the proximal end and a second lower flexural modulus proximate the distal end. Optionally, the graduated strain relief fitting includes a first flexural modulus proximate the proximal end of the fitting greater than a flexural modulus of the catheter shaft to minimize shaft kinking at the hub interface. The graduated strain relief fitting includes a second flexural modulus proximate the distal end of the fitting less than or equal to the flexural modulus of the catheter shaft to permit deflection of the catheter shaft (near to the distal end) while minimizing sharp stress risers that otherwise promote kinking.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The Drawings illustrate generally, by way of example, but not by way of limitation, various embodiments discussed in the present document.

FIG. 4A is a cross sectional view of the graduated strain relief fitting of FIG. 1.

FIG. 4B is a cross sectional view of another example of a graduated strain relief fitting including a plurality of fitting materials.

DETAILED DESCRIPTION

Figure 1:
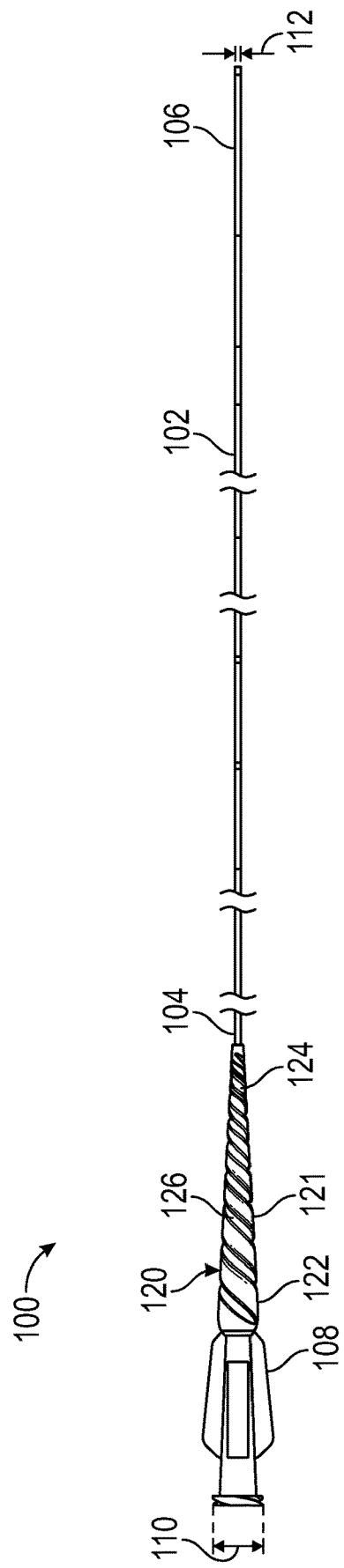
FIG. 1 is a perspective view of one example of a catheter assembly including a graduated strain relief fitting.

FIG. 1 shows one example of a catheter assembly 100 having a hub 108 coupled with a catheter shaft 102. As further shown in FIG. 1, a graduated strain relief fitting 120 is interposed between at least a portion of the hub 108 and the catheter shaft 102.

As further shown in MG. 1, the graduated strain relief fitting 120 includes a fitting body 121. constructed with one or more of polymers, metals, composites or the like. The graduated strain relief fitting 120 (e.g., the fitting body 121) extends from a fitting proximal portion 122 to a fitting distal portion 124. The fitting proximal portion 122 is coupled along with the hub 108 to interface with the hub 108 and accordingly minimize (e.g., lower, reduce or eliminate) stress risers therebetween. The fitting distal portion 124 provides a fitting interface between the graduated strain relief fitting 120 and the catheter shaft 102. For instance, in one example, the fitting distal portion 124 and a corresponding portion of the catheter shaft 102, such as a shaft proximal portion 104, include the fitting interface. The fitting distal portion 124 of the graduated strain relief fitting 120, as described herein, is configured to minimize (e.g., lower, reduce or eliminate) stress risers otherwise incident between the catheter shaft 102 and the interface with the graduated strain relief fitting 120 during navigation, deflection or manipulation of the catheter assembly 100.

Referring again to FIG. 1, the catheter shaft 102 extends from the shaft proximal portion 104 to the shaft distal portion 106. As shown in FIG. 1, the catheter shaft 102, in this example, has a shaft profile 112 smaller than a corresponding hub profile 110 of the hub 108. As further described herein, the graduated strain relief fitting 120 minimizes stress risers, for instance, between the hub 108 and the catheter shaft 102. In one example, the gradated strain relief fitting 120 includes a tapered profile configured to transition the catheter assembly 100 from the hub 108 (and the larger hub profile 110) to the shaft 102 (and the smaller shaft profile 112).

Additionally, and as described herein, the graduated strain relief fitting 120 minimizes (e.g., lowers, decreases or eliminates) stress risers at the interfaces between the fitting proximal portion 122 and the hub 108 (a hub interface) as well as at the fitting distal portion 124 and the catheter shaft 102 (a fitting interface). The graduated strain relief fitting 120 includes one or more flexure joints 126 configured to modulate (e.g., control, tune, graduate or the like) one or more support characteristics, such as flexural modulus, of the graduated strain relief fitting 120 to provide a specified flexibility to the graduated strain relief fitting 120 that maintains the support provided to the catheter shaft 102 at the interfaces with the fitting distal portion 124 as well as the interface with the hub 108, for instance, at the fitting proximal portion 122. Accordingly, the graduated strain relief fitting 120, including the flexure joints 126, provides a specified modulated flexural modulus at each of these interfaces and along the graduated strain relief fitting 120 to control the one or more support characteristics (e.g., flexural modulus, elastic modulus, tensile modulus or the like) to minimize kinking, buckling or the like of the catheter shaft 102, for instance, when deflected.

In the view shown in FIG. 1, the one or more flexure joints 126 include a helical groove, scallop or the like extending along the graduated strain relief fitting 120. In the example shown the one or more flexure joints 126 extend between the fitting proximal portion 122 and the fitting distal portion 124. As described herein, the one or more flexure joints 126 include, but are not limited to, grooves, scallops, scoring, flutes, notches, recesses, dimples or the like provided at one or more locations along the graduated strain relief fitting 120. For instance, the flexure joints 126 are provided at one or more locations or pitches (e.g., frequencies, joints per unit length or the like) to provide enhanced flexibility to the graduated strain relief fitting 120 at a specified location or locations. In another example, the flexure joints 126 are provided at one or more profiles, for instance, having a same or similar shape but one or more larger or smaller sizes to accordingly modulate the flexural modulus of the graduated strain relief fitting 120 at specified locations. In still other examples, the profiles of the flexure joints 126 include a variety of profiles (e.g., shapes, sizes, depth relative to the fitting surface, combinations of the same or the like) that modulate the flexural modulus of the fitting 120 at one or more specified locations.

Figure 2:
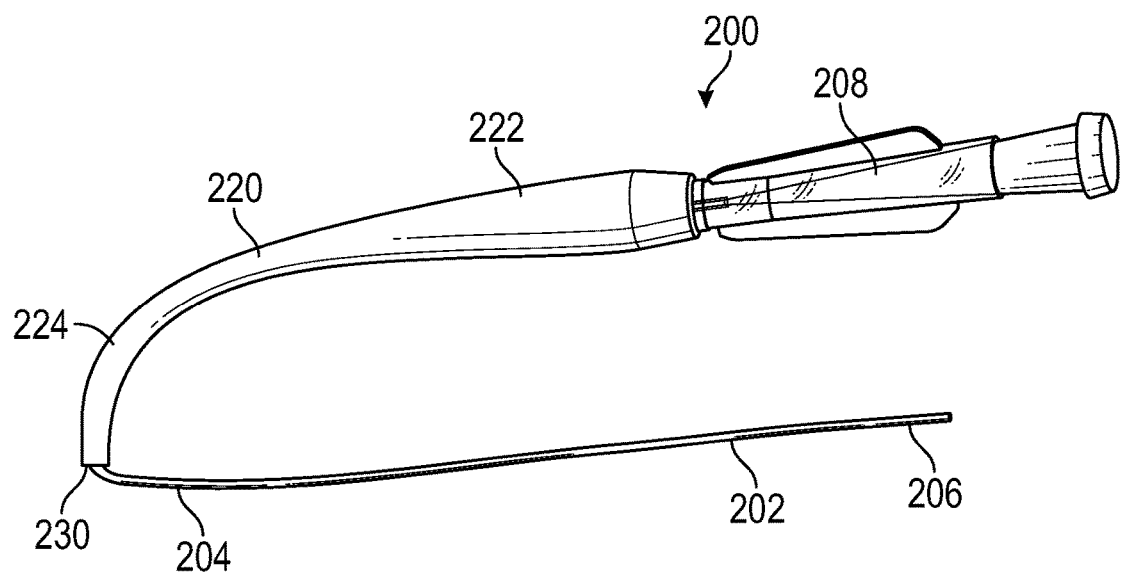
FIG. 2 is a side view of another example of a catheter assembly in a deflected configuration including a stress riser.

FIG. 2 shows another catheter assembly 200. In this example, the catheter assembly 200 includes a hub 208 coupled with a catheter shaft 202. A strain relief fitting 220 is interposed between the hub 208 and the catheter shaft 202. The strain relief fitting 220 includes a tapered configuration extending from a fitting proximal portion 222 to a fitting distal portion 224. As shown, the shaft proximal portion 204 extends to a shaft distal portion 206. In one example, the shaft proximal portion 204 extends within the strain relief fitting 220 and is coupled with the hub 208.

The catheter assembly 200 in FIG. 2 is in a deflected configuration, for instance, with one or more of lateral deflections, twisting or the like of the catheter shaft 202 relative to the hub 208. A stress riser 230 is included at the interface between the fitting distal portion 224 and the shaft proximal portion 204. In the example shown the stress riser 230 kinks the catheter shaft 202 at the interface between the fitting distal portion 224 and the shaft proximal portion 204. In some examples, the support characteristic of the strain relief fitting 220 at the fitting distal portion 224 provides a robust strain relief fitting 220 that supports the catheter shaft 202 proximal to the fitting distal portion 224. The remainder of the catheter shaft 202 extending to the shaft distal portion 206 is without this support. Accordingly, with deflection of the catheter shaft 202 a stress riser 230 is imparted to the catheter shaft 202 at the interface of the fitting distal portion and the shaft proximal portion 204. The stress 230 causes kinking at the interface between the fitting distal portion 224 and the shaft proximal portion 204. In one example, the flexural modulus of the fitting distal portion 224 is greater than the corresponding flexural modulus of the catheter shaft 202. Accordingly, when the catheter assembly 200 is deflected the fitting distal portion 224 deflects to a limited degree while the catheter shaft 202 bends, kinks or the like in a more pronounced fashion relative to the fitting distal portion.

Figure 3:
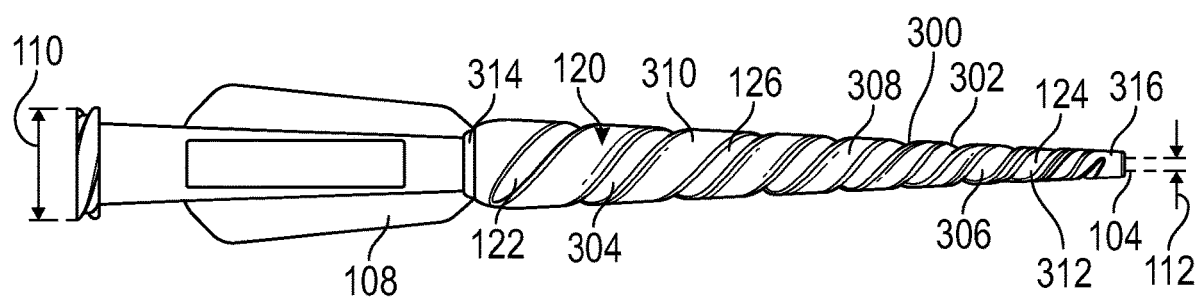
FIG. 3 is a side view of the graduated strain relief fitting of FIG. 1.

FIG. 3 shows a detailed side view of the hub 108 and the graduated strain relief fitting 120 previously shown in FIG. 1, As shown, the graduated strain relief fitting 120 extends from the hub 108, for instance, from a hub interface 314 proximate the huh 108 to a fitting interface 316 proximate the shaft proximal portion 104 extending from the fitting 120. The shaft proximal portion 104 extends within the strain relief fitting 120 to the hub 108. In one example, the catheter shaft is received and coupled with the hub 108 within an interior orifice of the hub 108. The graduated strain relief fitting 120 provides the hub interface 314 and the fitting interface 316.

As shown in FIG. 3, the graduated strain relief fitting 120 includes one or more flexure joints 126 provided along the fitting 120, For instance, a strain relief profile 300 of the flexure joints 126 includes, but is not limited to, one or more of grooves, scallops, scoring, flutes, notches, recesses, dimples or the like along the graduated strain relief fitting 120. In this example, the strain relief profile 300 extends from the fitting proximal portion 122 to the fitting distal portion 124. In another example, the strain relief profile 300 is located at one or more specified locations of the fitting 120, for instance proximate to the fitting distal portion 124, one or more other locations of the fitting or the like.

In one example, the strain relief profile 300 is a consistent profile extending between the fitting proximal and distal portions 122, 124. In another example, the strain relief profile 300 changes from the fitting proximal portion 122 to the fitting distal portion 124. For instance, one or more of the shape, size, frequency or the like of the flexure joint 126 changes between the proximal and distal portions 122, 124. In the example shown in FIG. 3, a first joint pitch 304, for instance, the number of flexure joints 126 per unit length is less than a second joint pitch 306 proximate to the fitting distal portion 124. The increase in joint pitch (e.g., the second joint pitch 306 in this example) decreases the wall thickness of the graduated strain relief fitting 120 at the fitting distal portion 124 and the fitting interface 316. The increase in joint pitch modulates the support characteristic of the fitting 120 at the fitting interface 316, for instance to a value similar to the support characteristic (e.g., flexural modulus) of the shaft proximal portion 104. In this example, the flexural modulus of the fitting distal portion 124 more closely approximates the flexural modulus of the shaft proximal portion 104. As described herein, by controlling a support characteristic such as flexural modulus at the fitting distal portion 124 the fitting distal portion 124 readily deflects with the shaft proximal portion 104 while at the same time also supporting the shaft proximal portion 104 under deflection. Accordingly, one or more of kinking, buckling, underlying stress risers or the like are minimized at the fitting interface 316 between the fitting distal portion 124 and the shaft proximal portion 104.

In another example, the graduated strain relief fitting 120 includes a fitting frame 308 between the one or more flexure joints 126. The fitting frame 308 is, in one example, a portion of the graduated strain relief fitting 120 having a wall thickness greater than the corresponding wall thickness proximate to the flexure joints 126. Accordingly, the fitting frame 308 provides enhanced support to one or more portions of the graduated strain relief fitting 120 while the flexure joints 126 modulate the support provided by the graduated strain relief fitting 120. Changes in one or more of the frequency of the fitting frame 308, frequency of the flexure joints 126 or the like are used in various examples to provide one or more specified support characteristics, such as flexural modulus, at one or more locations of the graduated strain relief fitting 120 to correspondingly support the catheter shaft 102 during deflection while at the same time minimizing stress risers, kinking, buckling or the like.

In the example shown in FIG. 3, the fitting frame 308 includes a first frame pitch 310 proximate to the fitting proximal portion 122 that is greater relative to a second frame pitch 312 associated with the fitting distal portion 124. With the greater first frame pitch 310 (e.g., frequency, area or length of the frame per unit length or the like) proximate to the fitting proximal portion 122, the support provided by the graduated strain relief fitting 120 is accordingly enhanced relative to the lesser second frame pitch 312, for instance, proximate to the fitting distal portion 124.

In another example, the graduated strain relief fitting 120 includes a taper between the fitting proximal and distal portions 122, 124. As shown in FIG. 3, the fitting 120 tapers toward the distal portion 124. The taper of the graduated strain relief fitting 120 is another example of a feature configured to modulate the support characteristics of the fitting, for instance to provide support to the catheter shaft 102 and at the same minimize stress risers, kinking, buckling or the like. For example, the wall thickness of the graduated strain relief fitting (including the fitting body 121, FIG. 1) is gradually decreased from the fitting proximal and distal portions 122, 124 to accordingly permit enhanced deflection proximate to the distal portion 122 while supporting the catheter shaft 102. In still another example, the taper cooperates with the features described herein including one or more of flexure joints 126, fitting frame 308, variations in the same or the like to modulate one or more support characteristics of the fitting 120 at one or more locations (e.g., along the catheter shaft 102, proximate to the hub 108 or the like).

FIG. 4A shows a cross-sectional view of an example graduated strain relief fitting 120. In this example, the hub 108 is a varied configuration or profile relative to the hub 108 previously shown in FIG. 3. As shown in FIG. 4A a portion of the hub 108 is received within a hub socket 404 of the graduated strain relief fitting 120. Similarly, the catheter shaft 102 is received within a shaft channel 406 of the graduated strain relief fitting 120. As further shown in FIG. 4A a portion of the shaft proximal portion 104 is received within a corresponding portion of the hub 108. The hub 108 optionally includes a channel, port or the like configured to receive the shaft proximal portion 104 therein. Accordingly, in this example, the catheter shaft 102 extends through the fitting distal portion 124 along the shaft channel 406 through the fitting proximal portion 122 and into the hub 108.

As further shown in FIG. 4A, the graduated strain relief fitting 120 includes the strain relief profile 300 having one or more of the flexure joints 126 and intervening portions of the graduated strain relief fitting 120, for instance, corresponding to the fitting frame 308 shown in FIG. 3. As shown in FIG. 4A, a first wall thickness 400 corresponding, for instance, to the wall thickness provided proximate to the flexure joints 126 is less than a corresponding second wall thickness 402 provided between the flexure joints 126 in the fitting frame 308. The second wall thickness 402, in one example, corresponds to the wall thickness of the fitting frame 308 between the flexure joints 126. As further shown in FIG. 4A, the second wall thickness 402 and the associated fitting frame 308 assume a larger proportion of the overall strain relief profile 300 proximate to the fitting proximal portion 122. Conversely, the first wall thickness 400 and the associated flexure joints 126 proximate to the fitting distal portion 124 assume a larger portion of the strain relief profile 300. As previously described with regard to FIG. 3, the variation in the fitting frame 308 as well as the flexure joints 126 including, for instance, various changes in profiles of the flexure joints 126 or fitting frame 308, frequencies (e.g., pitch) or the like modulates the support provided by the graduated strain relief fitting 120 in a specified manner.

In the example shown in FIG. 4A, by providing additional flexure joints 126, a higher frequency of flexure joints (second joint pitch 306 in FIG. 3) and a corresponding lower frequency of the fitting frame (second frame pitch 312) proximate to the fitting distal portion 124, the support characteristic provided by the fitting distal portion 124 is decreased, for instance, to correspond with or closely approximate one or more mechanical characteristics of the shaft proximal portion 104 including, for instance, a flexural modulus of the catheter shaft 102.

Conversely, the ratio of the fitting frame 308 to the flexure joints 126 including, for instance, a first frame pitch 310 and a first joint pitch 304 (as shown in FIG. 3) is modulated at the fitting proximal portion 122 to accordingly bolster or enhance the support characteristics of the graduated strain relief fitting 120 proximate to the hub interface 314, and thereby minimize a sharp decrease of the support characteristic at the hub interface 314 relative to the robust material of the hub 108. Accordingly, by modulating the support provided at the hub interface 314 and the fitting interface 316, the support characteristics of the graduated strain relief fitting 120 are modulated or tuned to correspond to the structural specifications of the shaft proximal portion 104 at a plurality of locations. The graduated strain relief fitting thereby minimizes kinking, buckling, stress risers or the like while at the same time providing support at each of the hub interface 314 and the fitting interface 316.

FIG. 4B is another cross-sectional view of a graduated strain relief fitting 410 of a catheter assembly. The graduated strain relief fitting 410, shown in FIG. 4B, is similar in at least some regards to the graduated strain relief fitting 120 shown in FIG. 4A. For instance, the fitting 410 includes a hub socket 404 configured for reception of a portion of a hub 108 therein. A shaft channel 406 extends through the strain relief fitting 410 and is concentric with a corresponding orifice within the hub 108. Additionally, the catheter shaft 102 extends through the graduated strain relief fitting 410 along the shaft channel 406 and is received in the hub socket 404. As further shown in FIG. 4B, the graduated strain relief fitting 410 includes a strain relief profile 300 including one or more flexure joints 126, a fitting frame 308 or the like between the fitting proximal portion 122 and the fitting distal portion 124. As previously described, the fitting frame 308 and flexure joints 126 cooperate with the material of the graduated strain relief fitting 410 to modulate (e.g., control, tune, modify or the like) the support characteristics of the graduated strain relief fitting 410, for instance, at one or more of the hub interface 314 and the fitting interface 316.

As further shown in this example, the graduated strain relief fitting 410 includes one or more fitting materials, such as a first fitting material 412 and a second fitting material 414. The first fitting material 412 includes a higher support characteristic (e.g., flexural modulus, tensile modulus, rigidity or the like) relative to the second fitting material 414 associated with a fitting distal portion 124. Accordingly, the second fitting material 414 provides a more flexible distal portion 124 to correspond and flexibly support the shaft proximal portion 104 at the fitting interface 316. Conversely, the first fitting material 412 associated with the fitting proximal portion 122 has a higher support characteristic (e.g., flexural modulus, tensile modulus, rigidity or the like) than the fitting distal portion 124. Accordingly, additional support is provided at the hub interface 314 to the catheter shaft 102 to maintain the catheter shaft 102 in a relatively linear configuration relative to the hub 108 at the hub interface 314.

In another example, the graduated strain relief fitting 410 includes one or more supplemental materials including, for instance, a third fitting material 416, for instance, interposed between the first and second fitting materials 412, 414. In one example, the third fitting material 416 is a more flexible material than that used in the first fitting material 412 and a less flexible material than the second fitting material 414. For instance, the third fitting material 416 provides an intermediate support characteristic (e.g., flexural modulus or the like) relative to the flexural moduli of the fitting proximal and distal portions 122, 124. In still other examples, the fitting materials 412, 414, 416 include the same material, and the material is selectively doped or treated to provide differing support characteristics. For instance, the first fitting material 412 includes a fitting filler including, but not limited to, metallic particles, glass fibers or the like configured to enhanced the support characteristic of the first fitting material 412 and the associated fitting proximal portion 122. In this example, the second fitting material 414 includes a lesser amount of the fitting filler (including no filler) to provide a flexible fitting distal portion 124 to conform or provide a complementary profile of the graduated strain relief fitting 410 to the catheter shaft (see FIG. 5). In another example, the fitting filler includes one or more materials, reticulations, pores or the like that decrease the support characteristic and enhance the flexibility. In this permutation additional fitting filler is provided with the second fitting material 414 to enhance flexibility while still providing support, and a lesser amount of the fitting filler is provided in the first fitting material 412 to enhance support while decreasing flexibility.

Figure 5:
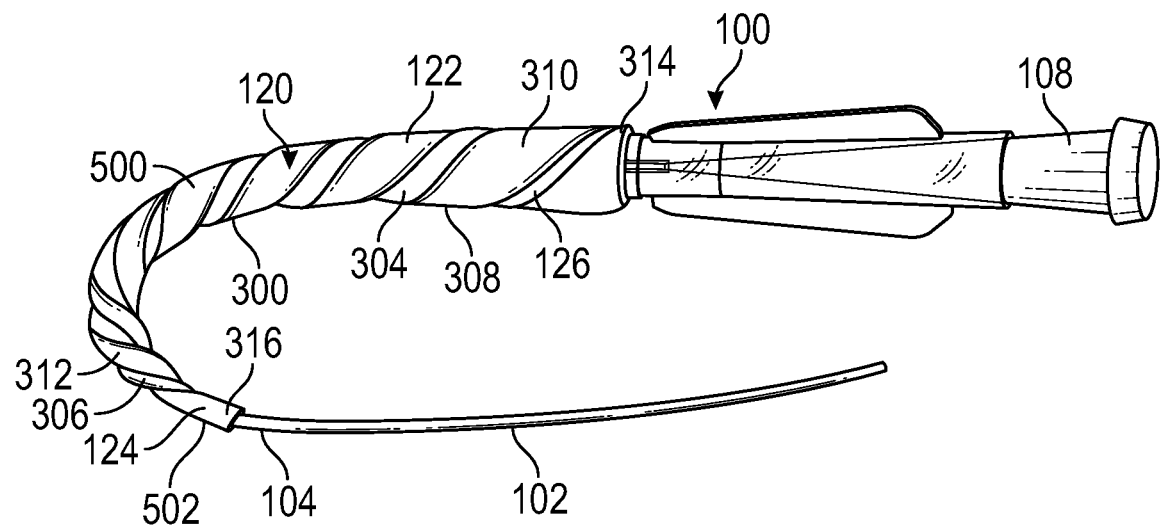
FIG. 5 is a side view of the catheter assembly of FIG. 1 in a deflected configuration with the graduated strain relief fitting having a complementary profile to the deflected catheter shaft.

FIG. 5 shows the catheter assembly 100 including the graduated strain relief fitting 410. Optionally, the catheter assembly 100, shown in FIG. 5, is used with the graduated strain relief fitting 400 shown in FIG. 4B (including, for instance, one or more of variations in material, profile, both or the like). Referring again to FIG. 5, the catheter assembly 100 is shown in a deflected configuration 500 including one or more of bending or twisting of the catheter shaft 102. As shown, the graduated strain relief fitting 120 assumes a complementary profile 502 to the deflected catheter shaft 102 in contrast to the configuration shown in FIG. 2 including the stress riser 230 and corresponding kink in the catheter shaft 202.

As previously described, the graduated strain relief fitting 120 includes one or more of flexure joints 126, a fitting frame 308, variations in material or the like. The fitting 120, including one or more of these features, is configured to provide one or more supporting characteristics to the catheter shaft 102, for instance at the hub interface 314 between the graduated strain relief fitting 120 and the hub 108 and the fitting interface 316 between the fitting distal portion 124 of the strain relief fitting 120 and the shaft proximal portion 104. As shown in FIG. 5, the shaft proximal portion 104 is in a deflected curved configuration. In contrast to FIG. 2, the catheter assembly 100, shown in FIG. 5, includes the catheter shaft 102 in the deflected configuration 500 without kinks, buckling or the like. Instead, the strain relief fitting 120 provides a complementary profile 502 to the deflected catheter shaft 102.

The fitting distal portion 124 includes a support characteristic configured to provide flexibility in the fitting distal portion 124 while at the same time supporting the shaft proximal portion 104 in the deflected configuration 500. For example, the flexure joints 126, joint pitch, fitting frame 308, frame pitch, materials or the like are configured to provide a specified support characteristic at the fitting distal portion 124 including the fitting interface 316. The support characteristic (e.g., a second flexural modulus) is modulated proximate to the fitting distal portion 124 relative to a first higher flexural modulus of the fitting proximal portion 122 with one or more of variations in the flexure joints 126, fitting frame 308, their respective pitches, materials of the fitting or the like. The modulated support characteristic of the fitting distal portion 124 permits deflection of the catheter shaft 102 and the fitting distal portion 124 into a configuration and respective complementary profile 502 like that shown in FIG. 5. At the same time the graduated strain relief fitting 120 having the complementary profile 502 also supports the catheter shaft 102 while deflected to minimize (e.g., decreasing, eliminating or the like) events that complicate procedures, such as kinking or buckling of the catheter shaft 102.

Conversely, the fitting proximal portion 122 including, for instance, one or more of a thicker wall, an increased frame pitch 310 relative to the frame pitch 312, decreased joint pitch 304 relative to the joint pitch 306, variations in material or the like provides enhanced support to the catheter shaft 102 proximate to the hub interface 314. Accordingly, the catheter shaft 102 remains in a substantially linear configuration relative to the hub 108 even in the deflected configuration 500. In one example, the support characteristic of the fitting proximal portion 122, such as a first flexural modulus, is greater than the second flexural modulus at the fitting distal portion 124. Optionally, the flexural modulus of the proximal portion 122 approaches a corresponding flexural modulus of the hub 108.

The graduated strain relief fitting 120, including one or more of the flexure joints 126 (e.g., grooves, scallops, scoring, flutes, notches, recesses, dimples or the like), the fitting frame 308, modulation of their respective profiles or pitch, as well as variations in material are used separately or together to modulate the support characteristics of the graduated strain relief fitting 120 to accordingly provide enhanced support characteristics at one or more locations while permitting deflection of the catheter shaft (and optionally assuming the complementary profile 502).

In one example, the second flexural modulus of the fitting distal portion 124 includes a flexural modulus less than or equal to the flexural modulus of the catheter shaft 102 to support the catheter shaft and assume the complementary profile 502. In another example, the second flexural modulus of the fitting distal portion 124 approaches the flexural modulus of the catheter shaft 102. For instance, the second flexural modulus substantially matches the modulus of the catheter shaft (e.g., is equal to or within 1 to 5 percent above or below the modulus, within 1000, 5000, 10,000 psi or the like). In another example, the fitting proximal portion 122 includes a first flexural modulus greater than the flexural modulus of the fitting distal portion 124 and accordingly greater than the flexural modulus of the catheter shaft 102. The first flexural modulus optionally approaches the modulus of the hub 108 (e.g., is equal to or within 20 to 25 percent of the hub modulus, within 10,000, 20,000 or 50,000 psi or the like). In one example, with these modulated support characteristics the graduated strain relief fitting 120 is configured to assume the complementary profile 502 in the deflected configuration 500 and support the catheter shaft 102 while at the same time minimizing one or more of kinking, buckling or the like. Optionally, flexural modulus as used herein is used interchangeably with similar mechanical characteristics, such as modulus of elasticity (Young's modulus), tensile strength or the like.

Figure 6A:
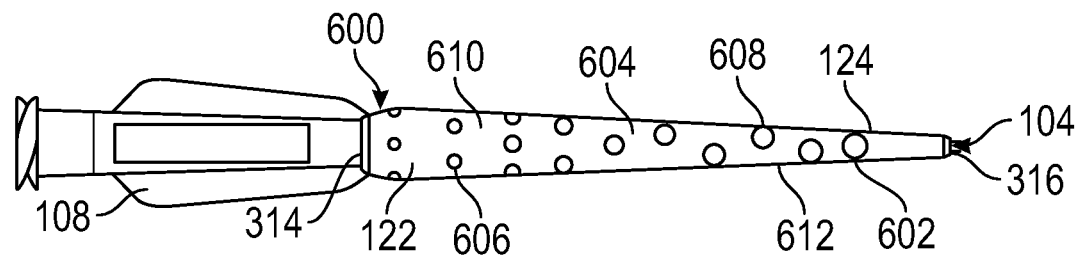
FIG. 6A is a detailed side view of another example of a graduated strain relief fitting.

FIGS. 6A-D show examples of graduated strain relief fittings 600, 620, 640, 660. In each of these examples, the strain relief fittings include one or more flexure joints, fitting frames, pitches (e.g., frequency of the flexure joints, fitting frame or the like) to illustrate example variations of these features useable with the graduated strain relief fittings described herein. Referring first to FIG. 6A, the example graduated strain relief fitting 600 includes one or more features similar to the previously described strain relief fitting, such as the fitting 120. For instance, the strain relief fitting 600 is coupled with a hub 108 at a hub interface 314 and is coupled with a shaft proximal portion 104 of the catheter shaft. As further shown in FIG. 6A, a fitting interface 316 is between the fitting distal portion 124 of the graduated strain relief fitting 600 and the shaft proximal portion 104. Conversely, the hub interface 314 is between the fitting proximal portion 122 and the hub 108.

Referring again to FIG. 6A, the graduated strain relief fitting 600 includes one or more flexure joints 602 between the fitting proximal and distal portions 122, 124. In this example, the flexure joints 602 include scallops, recesses, dimples or the like provided along the graduated strain relief fitting 600. As shown in FIG. 6A, the flexure joints 602 have an increasing profile (in this example, size), from the fitting proximal portion 122 to the fitting distal portion 124. For instance, the flexure joints 602 provided proximate to the fitting proximal portion 122 are smaller than those proximate to the fitting distal portion 124. Conversely, the fitting frame 604 is between the flexure joints 602 from the fitting proximal portion 122 to the fitting distal portion 124. In this example, the fitting frame 604 increases, for instance, has a greater surface area (per unit length) as the graduated strain relief fitting 600 extends from the fitting distal portion 124 to the fitting proximal portion 122.

As further shown in FIG. 6A, in this example, first and second frame pitches 610, 612 of the fitting frame 604, conversely decrease between the fitting proximal portion 122 and the fitting distal portion 124. As shown in FIG. 6A, the frame pitches include intervening space between flexure joints corresponding to portions of the fitting 120 having an increased wall thickness relative to proximate flexure joints 602. The first frame pitch 610 proximate to the fitting proximal portion 122 is larger than the second frame pitch 612 proximate the fitting distal portion 124. Accordingly, as the frame pitch decreases toward the fitting distal portion 124 (and the joint pitch increases to the pitch 608) the graduated strain relief fitting 600 provides enhanced flexibility proximate to the fitting distal portion.

As further shown in FIG. 6A, in this example, first and second frame pitches 610, 612 of the fitting frame 604, conversely decrease between the fitting proximal portion 122 and the fitting distal portion 124. As shown in FIG. 6A, the frame pitches include intervening space between flexure joints corresponding to portions of the fitting 120 having an increased wall thickness relative to proximate flexure joints 602. The first frame pitch 610 proximate to the fitting proximal portion 122 is larger than the second frame pitch 612 proximate the fitting distal portion 124. Accordingly, as the frame pitch decreases toward the fitting distal portion 124 (and the joint pitch increases to the fit 608) the graduated strain relief fitting 600 provides enhanced flexibility proximate to the fitting distal portion.

Conversely, the graduated strain relief fitting 600 provides enhanced support proximate to the fitting proximal portion 122 according to the first frame pitch 610 (and counterpart first joint pitch 606) relative to the second frame pitch 612 (and counterpart second joint pitch 608) at the fitting distal portion 124. Accordingly, the fitting distal portion 124 provides a support characteristic for the shaft proximal portion 104 configured to facilitate bending of the shaft proximal portion 104 but at the same time support the shaft proximal portion 104 and minimize (e.g., decrease, eliminate or the like), kinking, buckling or the like of the shaft. One example of the deformation is shown in the deflected configuration 500 in FIG. 5 including the complementary profile 502.

Optionally, the fitting distal portion 124, including variations in the flexure joints 602 and fitting frame 604, provide a support characteristic, such as flexural modulus, approximating the flexural modulus of the catheter shaft 102. In another example, the flexural modulus of the fitting distal portion 124 of the graduated strain relief fitting 600 includes a flexural modulus less than or equal to the flexural modulus of the catheter shaft 102. The flexural modulus of the fitting distal portion 124, when approximating the catheter shaft 102 (equal to or less than, within 1 to 5 percent of the catheter shaft or the like) facilitates the supported deformation of the catheter shaft 102 while the fitting 600 assumes a supporting complementary profile, such as the profile 502, shown in FIG. 5.

Figure 6B:
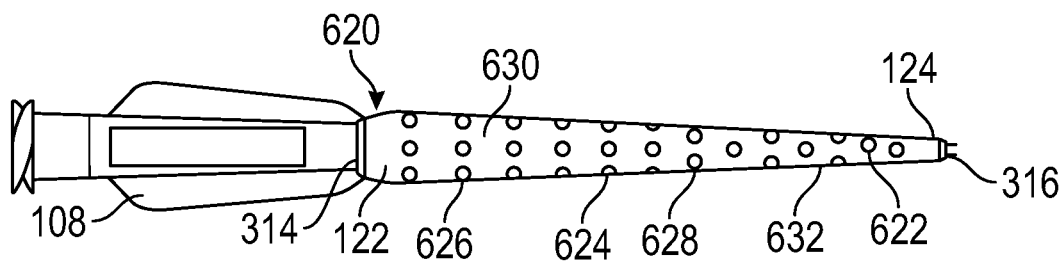
FIG. 6B is a detailed side view of an additional example of a graduated strain relief fitting.

FIG. 6B shows another example of a graduated strain relief fitting 620. In this example, the flexure joints 622 of the strain relief fitting 620 have a consistent profile while providing another example of a variation in pitch. For instance, the scallops, recesses, dimples or the like provided along the graduated strain relief fitting 620 have a consistent shape and size. In contrast, the joint pitch of the flexure joints 622 (e.g., frequency, number of flexure joints per unit length or the like) increases from the fitting proximal portion 122 to the fitting distal portion 124 of the fitting 620. Accordingly, with additional flexure joints 622 proximate to the fitting distal portion 124, the profile of the graduated strain relief fitting 620 has an enhanced recessed configuration proximate to the fitting distal portion 124. Conversely, the fitting frame 624 interposed between the flexure joint 622 in this example has an increased surface area (an example of frame pitch) proximate to the fitting proximal portion 122.

As further shown in FIG. 6B, the first joint pitch 626 with the consistent profile flexure joints 622 is less than the second joint pitch 628 proximate the fitting distal portion 124. Conversely, the first frame pitch 630 proximate to the fitting proximal portion 122 is greater in comparison to the second frame pitch 632 proximate to the fitting distal portion 124. As shown in FIG. 6B, the relationship between the various pitches is optionally similar to the pitches shown in FIG. 6A. For example, the frame pitch gradually decreases from the proximal to the distal portions 124, while the joint pitch gradually increases. Accordingly, the fitting distal portion 124 provides support to the shaft proximal portion 104 while at the same time flexibly deforming with deflection of the shaft proximal portion 104, for instance, into a complementary configuration, such as the configuration 502 shown in FIG. 5.

Figure 6C:
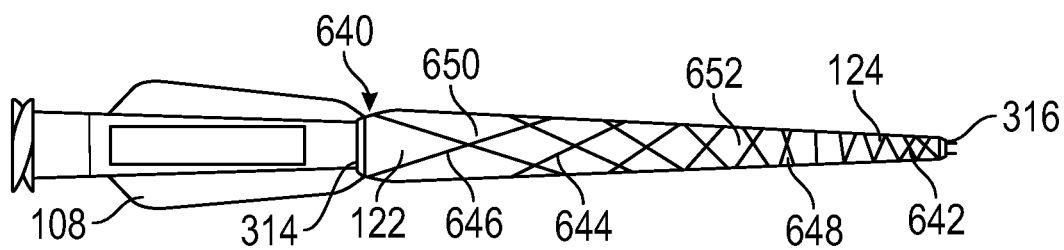
FIG. 6C is a detailed side view of a supplemental example of a graduated strain relief fitting.

FIG. 6C shows another example of a graduated strain relief fitting 640. In this example, the flexure joints 642 include, but are not limited to, one or more grooves, scallops, scoring, flutes, notches or the like provided along the graduated strain relief fitting 640. For instance, the flexure joints 642 include one or more grooves or scoring provided at angles, orientations or the like along the graduated strain relief fitting 640 to modulate the support characteristics of the strain relief fitting 640 between the fitting proximal and distal portions 122, 124. For instance, as shown in FIG. 6C, the first joint pitch 646 and the second joint pitch 648 of the fitting proximal and distal portions 122, 124 vary. In FIG. 6C the angles of the flexure joints (another example of joint pitch) decrease or approach a similar orientation to the longitudinal axis of the graduated strain relief fitting 640 as the flexure joints 642 progress toward the fitting proximal portion 122. Conversely, the flexure joints 642 have a greater pitch (e.g., angle, orientation relative to the longitudinal axis or the like) as the joints approach the fitting distal portion 124. Conversely, the fitting frame 644, in this example between the flexure joints 642 includes a greater first frame pitch 650 (e.g., area per unit length) proximate to the fitting proximal portion 122 relative to a second frame pitch 652 proximate to the fitting distal portion 124.

Figure 6D:
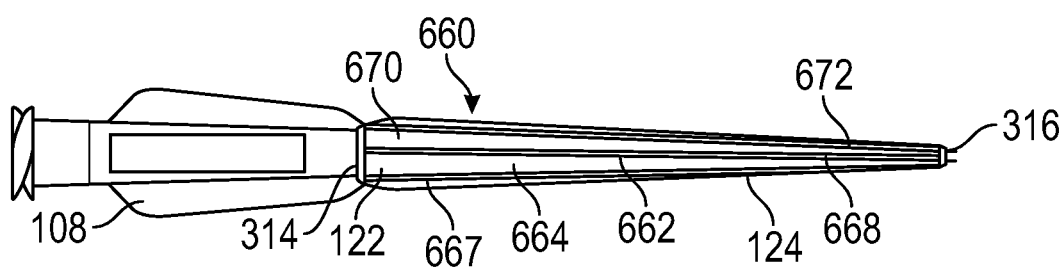
FIG. 6D is a detailed side view of yet another example of a graduated strain relief fitting.

FIG. 6D shows another example of a graduated strain relief fitting 660. In this example, the strain relief fitting 660 includes flexure joints 662 (gaps, grooves, scallops, recesses or the like) extending in a longitudinal fashion, for instance, along the strain relief fitting between the fitting proximal portion 122 and fitting distal portion 124. As shown in FIG. 6D, the flexure joints 662 have an angled configuration optionally corresponding to the taper of the graduated strain relief fitting 660. Accordingly, the first joint pitch 667 (in this example, ratio of joint area to frame area or the like) proximate to the fitting proximal portion 122 is less than the second joint pitch 668 proximate to the fitting distal portion 124. As shown in FIG. 6D, the flexure joints 662 are packed, clustered or the like proximate to the fitting distal portion 124. In contrast the flexure joints 662 proximate to the fitting proximal portion 124 are relatively spaced apart, and accordingly include the lesser first joint pitch 667.

Conversely, the pitch of the fitting frame 664 interposed between the flexure joints 662 decreases between the fitting distal and proximal portions 124, 122. Accordingly, the first frame pitch 670 (e.g., frame area per unit length, ratio of frame area to the joint area or the like) proximate to the fitting proximal portion 124 is greater than the second frame pitch 672 proximate to the fitting distal portion 124. In a similar manner to the other graduated strain relief fittings described herein, the flexure joints 662 and the fitting frame 664 cooperate to modulate the support characteristics of the graduated strain relief fitting 660, for instance, at the fitting interface 316 and the hub interface 314.

As shown in FIG. 6I), the fitting frame 664 having the higher first frame pitch 670 proximate to the fitting proximal portion 122 supports the hub interface 314 with the increased wall thickness of the frame relative to the joints 662. Conversely, the flexure joints 662 having a higher second joint pitch 668 (e.g., clustering, density or the like) proximate the fitting distal portion 124 enhance the flexibility of the graduated strain relief fitting 660 while, at the same time, providing support to the shaft proximal portion 104. As previously described, the modulation (tuning, varying, controlling or the like) of the support characteristics of the fitting, such as flexural moduli, facilitates the supported deformation of the catheter shaft such as the catheter shaft 102, shown in FIG. 5, into the example deflected configuration 500 including the example complementary profile 502 shown in FIG. 5. Stated another way, the shaft proximal portion 104 is readily deflected into the configuration 500 shown in FIG. 5 and at the same time is supported by the strain relief fitting 660 (as well as the other examples described herein) in a complementary profile.

Figure 7:
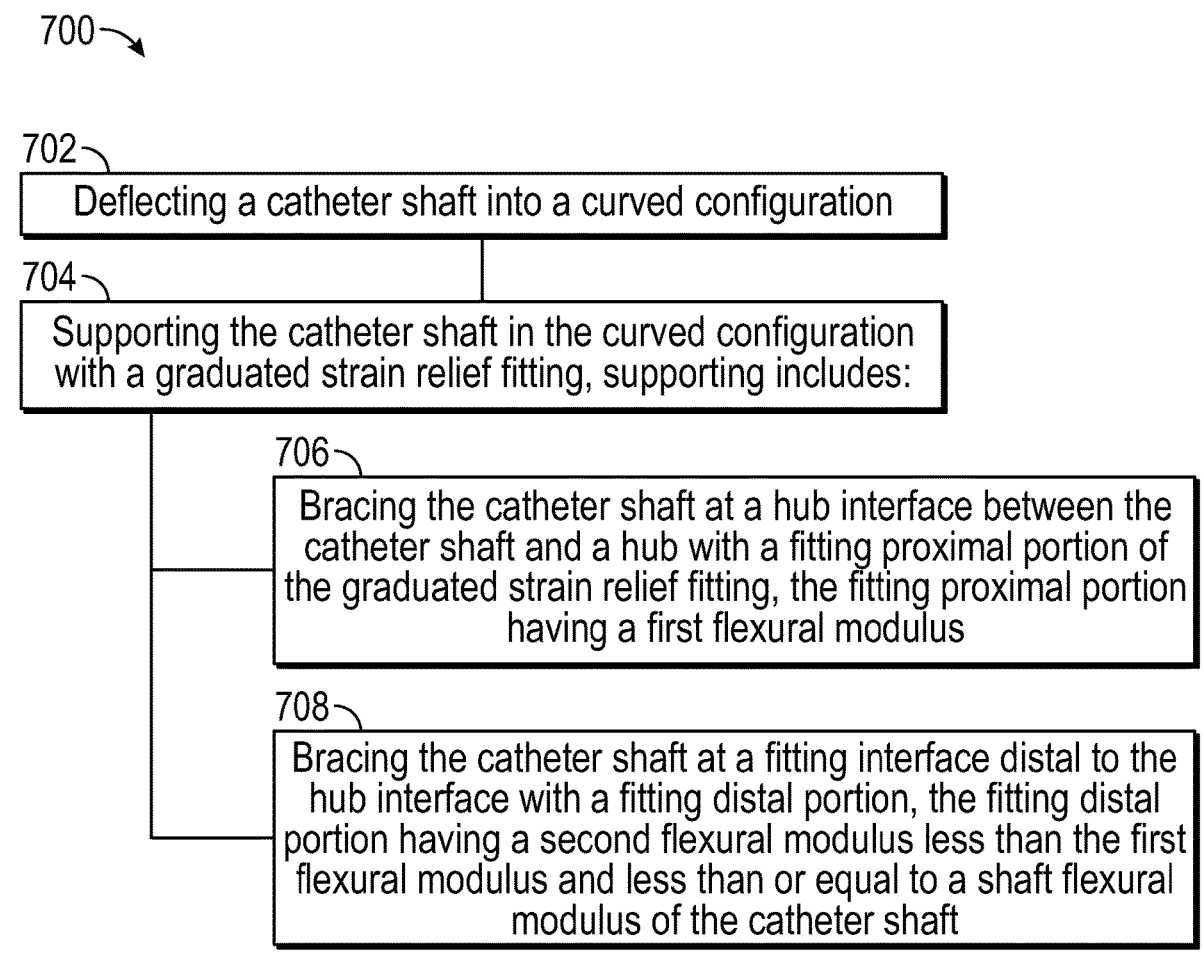
FIG. 7 is a block diagram showing one example of a method for using a catheter assembly.

FIG. 7 shows one example of a method 700 of supporting a catheter such as the catheter assembly 100 previously described and shown herein. In describing the method 700, reference is made to one or more components, features, functions or steps previously described herein. Where convenient, reference is made to the components, features, functions, steps or the like with reference numerals. Reference numerals provided are exemplary and are not exclusive. For instance, components, features, functions, steps or the like described in the method 700 include, but are not limited to, corresponding numbered elements provided herein, other corresponding features described herein (both numbered and unnumbered) as well as their equivalents.

At 702, the method 700 includes deflecting a catheter shaft, such as the catheter shaft 102 shown in FIG. 5 into a curved configuration including, but not limited to, the deflected configuration 500, bent, twisted or curved configurations or the like. Manipulation of the catheter assembly 100, for instance with rotation, lateral movement and axial movement, navigates the catheter shaft 102 through vasculature, anatomical passages or cavities or the like and deflects the catheter shaft 102 into one or more of these curved configurations to facilitate navigation.

The method 700 further includes at 704 supporting the catheter shaft 102 in the curved configuration (e.g., a deflected configuration) with a graduated strain relief fitting including one or more of the graduated strain relief fittings described herein. As previously described, the graduated strain relief fittings include modulated support characteristics, for instance, one or more flexural moduli at one or more locations of the fittings (e.g., the fitting proximal portion 122, the fitting distal portion 124, locations therebetween or the like). The graduated strain relief fittings having these support characteristics brace (support) the catheter shaft 102 while permitting deflection into deflected configurations.

At 706, supporting the catheter shaft 102 includes bracing the catheter shaft 102 at a hub interface, such as the hub interface 314 (see FIG. 5) between the shaft proximal portion 104 and the hub 108. For instance, a fitting proximal portion 122 of the graduated strain relief fitting 120 is coupled with the hub 108 and supports the catheter shaft 102 proximate to the hub interface 314. The fitting proximal portion 122 includes, for instance, a first flexural modulus (an example of a support characteristic) configured to support the shaft proximal portion 104 proximate the hub interface 314 and maintain the catheter shaft 102 in a linear or aligned configuration with the remainder of the hub 108. Optionally, the first flexural modulus approximates (e.g., approaches, is within range of or the like) a flexural modulus of the hub 108.

At 708, supporting of the catheter shaft 102 includes bracing the catheter shaft 102 at a fitting interface 316 distal to the hub interface 314. The fitting distal portion 124 is coupled with the shaft proximal portion 104. The fitting distal portion 124 of the graduated strain relief fitting 120 includes a second support characteristic, for instance, a second flexural modulus less than the first flexural modulus of the fitting proximal portion 122. In another example, the second flexural modulus is less than or equal to a shaft flexural modulus of the catheter shaft 102. With the second flexural modulus less than or equal to the shaft flexural modulus of the catheter shaft 102, the graduated strain relief fitting 120 is configured to assume a complementary profile 502 relative to the catheter shaft 102. Accordingly, the catheter shaft 102 readily bends, curves or the like into the configuration 500 shown in FIG. 5 while the graduated strain relief fitting 120 readily conforms to the deflection and supports the catheter shaft 102. The support of the strain relief fitting 120 thereby minimizes (e.g., minimizes, reduces or eliminates), kinking, buckling or the like of the catheter shaft 102.

In one example, supporting the catheter shaft 102 in the curved or deflected configuration 500 includes minimizing kinking or other structural complications of the catheter shaft 102 at each of the hub interface 314 and the fitting interface 316 according to the bracing of the catheter shaft at least at each of these locations. In another example, supporting the catheter shaft 102 includes bracing the catheter shaft between the hub and fitting interfaces 314, 316 with a graduated flexural modulus between the first and second flexural moduli of the fitting proximal and distal portions 122, 124. Optionally, bracing the catheter shaft 102 between the hub and fitting interfaces 314, 316 includes, in another example, continuously graduating the graduated flexural modulus or other support characteristic from the first flexural modulus to the second flexural modulus.

In one example, supporting the catheter shaft 102 with the graduated strain relief fitting 120 (and other fittings described and shown herein) includes controlling one or more support characteristics, such as the first and second flexural moduli, with one or more flexure joints 126, joint pitch (including profile, frequency or the like) of the flexure joints 126, fitting frames (and pitch) variations in fitting material or the like provided along the graduated strain relief fitting 120. Examples of flexure joints 126, joint pitch (as well as fitting frames and frame pitch), and fitting material are shown in FIGS. 1 and 3-6D. The flexure joints 126 include, but are not limited to, one or more of scallops, grooves, dimples, scoring, recesses, channels or the like provided along the graduated strain relief fitting. The flexure joints, joint pitch, fitting frames, frame pitch, variation in fitting material of the fitting modulate (e.g., tune, control, vary or the like) one or more support characteristics including one or more of the first or second flexural moduli.

In another example, controlling at least the first and second flexural moduli includes, in one example, increasing a joint pitch of the one or more flexure joints proximate to the fitting interface 316, for instance, relative to the hub interface 314. Joint pitch of the one or more flexure joints includes, but is not limited to, joint frequency or density (e.g., joints per unit length or area, ratio of joint area to fitting frame area), profile (size or shape), location or the like. One example of variation in joint pitch is shown in FIG. 3 and includes the first joint pitch 304 proximate the fitting proximal portion 122 and an increased second joint pitch 306 proximate the fitting distal portion 124. In another example, supporting the catheter shaft 102 includes, for instance, decreasing a frame pitch, for instance, of a fitting frame 308 between the fitting proximal portion 122 and the fitting distal portion 124. Frame pitch of the fitting frame includes, but is not limited to, fitting frame frequency or density (e.g., frame area per unit length, ratio of frame area to joint area), profile (size or, shape), location or the like. For instance, in FIG. 3, the frame pitch 312 proximate to the fitting distal portion 124 is less than the frame pitch 310 proximate to the fitting proximal portion 122.

In still another example, control of the support characteristics of the graduated strain relief fitting 120 includes, in another example, tapering of the graduated strain relief fitting, for instance, between the fitting proximal and distal portions 122, 124. Optionally, tapering of the graduated strain relief fitting includes controlling the wall thickness to modulate flexural modulus of the fitting or control the characteristics described herein along the graduated strain relief fitting 120.

In another example, supporting the catheter shaft 102 including controlling (e.g., modulating, tuning, varying or the like) the one or more support characteristics is achieved with control of the fitting material of the graduated strain relief fitting (controlling material composition, fitting fillers or the like). Optionally, the control of the fitting material includes one or more different fitting materials at locations along the graduated strain relief fitting 120. In another example, variation of fitting material includes the addition or subtraction of fitting filler of a base fitting material to accordingly modulate the support characteristics of the graduated strain relief fitting 120 (e.g., between the fitting proximal and distal portions 122, 124 and the corresponding interfaces).

Various Notes and Aspects

Aspect 1 can include subject matter such as a catheter assembly comprising: a catheter shaft extending between a shaft proximal portion and a shaft distal portion; a hub coupled with the catheter shaft proximate the shaft proximal portion, wherein the hub includes a hub profile larger than a shaft profile of the catheter shaft; and a graduated strain relief fitting coupled between the catheter shaft and the hub, the graduated strain relief fitting includes: at least a first flexural modulus proximate the hub and a fitting proximal portion; and at least a second flexural modulus proximate the catheter shaft and a fitting distal portion, the second flexural modulus is less than the first flexural modulus and less than or equal to a catheter shaft flexural modulus.

Aspect 2 can include, or can optionally be combined with the subject matter of Aspect 1, to optionally include wherein the graduated strain relief fitting includes one or more scalloped flexure joints between the fitting proximal and distal portions.

Aspect 3 can include, or can optionally be combined with the subject matter of one or any combination of Aspects 1 or 2 to optionally include wherein the graduated strain relief fitting includes a scalloped profile having the one or more scalloped flexure joints.

Aspect 4 can include, or can optionally be combined with the subject matter of one or any combination of Aspects 1-3 to optionally include wherein a first wall thickness of the graduated strain relief fitting proximate the one or more scalloped flexure joints is less than a second wall thickness of the remainder of the graduated strain relief fitting.

Aspect 5 can include, or can optionally be combined with the subject matter of one or any combination of Aspects 1-4 to optionally include wherein the one or more scalloped flexure joints include one or more channels, grooves, flutes, helical grooves, notches, recesses, dimples or scoring.

Aspect 6 can include, or can optionally be combined with the subject matter of Aspects 1-5 to optionally include wherein a first joint pitch of the scalloped flexure joints proximate the fitting proximal portion having the first flexural modulus is less than a second joint pitch at the fitting distal portion having the second flexural modulus.

Aspect 7 can include, or can optionally be combined with the subject matter of Aspects 1-6 to optionally include wherein the graduated strain relief fitting includes a fitting frame between the one or more scalloped flexure joints, and a first wall thickness proximate the fitting frame is greater than a second wall thickness proximate to the one or more scalloped flexure joints.

Aspect 8 can include, or can optionally be combined with the subject matter of Aspects 1-7 to optionally include wherein a first frame pitch of the fitting frame proximate to the fitting proximal portion is greater than a second frame pitch proximate to the fitting distal portion.

Aspect 9 can include, or can optionally be combined with the subject matter of Aspects 1-8 to optionally include wherein the graduated strain relief fitting includes at least one fitting material, and the fitting material proximate the fitting proximal portion provides the first flexural modulus, and the fitting material proximate the fitting distal portion provides the second flexural modulus.

Aspect 10 can include, or can optionally be combined with the subject matter of Aspects 1-9 to optionally include wherein the at least one fitting material includes a support filler, and the density of the support filler proximate the fitting proximal portion is greater than the density of the support filler proximate the fitting distal portion.

Aspect 11 can include, or can optionally be combined with the subject matter of Aspects 1-10 to optionally include wherein the at least one fitting material includes a graduated decreasing flexural modulus between the first flexural modulus proximate the fitting proximal portion and the second flexural modulus proximate the fitting distal portion.

Aspect 12 can include, or can optionally be combined with the subject matter of Aspects 1-11 to optionally include wherein the at least one fitting material includes at least first and second fitting materials, and the first fitting material is proximate the fitting proximal portion and the second fitting material is proximate the fitting distal portion.

Aspect 13 can include, or can optionally be combined with the subject matter of Aspects 1-12 to optionally include a catheter strain relief fitting comprising: a fitting body extend between a fitting proximal portion and a fitting distal portion, the fitting body includes: a hub socket configured for reception of a hub; and a shaft channel configured for reception of a catheter shaft; wherein the fitting body includes a graduated strain relief profile, the graduated strain relief profile includes: a taper extending between a hub interface proximate to the fitting proximal portion and a fitting interface proximate to the fitting distal portion; and one or more flexure joints between the fitting proximal and distal portions.

Aspect 14 can include, or can optionally be combined with the subject matter of Aspects 1-13 to optionally include wherein a flexural modulus of the fitting body decreases from proximate the fitting proximal portion to the fitting distal portion according to the graduated strain relief profile.

Aspect 15 can include, or can optionally be combined with the subject matter of Aspects 1-14 to optionally include wherein the flexural modulus of the fitting body continually decreases from proximate the fitting proximal portion to the fitting distal portion according to the graduated strain relief profile.

Aspect 16 can include, or can optionally be combined with the subject matter of Aspects 1-15 to optionally include wherein the fitting body includes: a first flexural modulus proximate the hub interface and the fitting proximal portion; and a second flexural modulus proximate the fitting interface and the fitting distal portion, the second flexural modulus is less than the first flexural modulus.

Aspect 17 can include, or can optionally be combined with the subject matter of Aspects 1-16 to optionally include wherein a first wall thickness of the fitting body proximate the one or more scalloped flexure joints is less than a second wall thickness of the remainder of the fitting body.

Aspect 18 can include, or can optionally be combined with the subject matter of Aspects 1-17 to optionally include wherein the one or more scalloped flexure joints include one or more helical grooves.

Aspect 19 can include, or can optionally be combined with the subject matter of Aspects 1-18 to optionally include wherein the one or more scalloped flexure joints include one or more channels, grooves, flutes, notches, recesses, dimples or scoring.

Aspect 20 can include, or can optionally be combined with the subject matter of Aspects 1-19 to optionally include wherein a first joint pitch of the scalloped flexure joints proximate the fitting proximal portion is less than a second joint pitch at the fitting distal portion.

Aspect 21 can include, or can optionally be combined with the subject matter of Aspects 1-20 to optionally include wherein the fitting body includes a fitting frame between the one or more scalloped flexure joints, and a first wall thickness proximate the fitting frame is greater than a second wall thickness proximate to the one or more scalloped flexure joints.

Aspect 22 can include, or can optionally be combined with the subject matter of Aspects 1-21 to optionally include wherein a first frame pitch of the fitting frame proximate to the fitting proximal portion is greater than a second frame pitch proximate to the fitting distal portion.

Aspect 23 can include, or can optionally be combined with the subject matter of Aspects 1-22 to optionally include wherein the fitting body includes at least one fitting material, and the fitting material proximate the fitting proximal portion provides a first flexural modulus, and the fitting material proximate the fitting distal portion provides a second flexural modulus.

Aspect 24 can include, or can optionally be combined with the subject matter of Aspects 1-23 to optionally include wherein the at least one fitting material includes a support filler, and the density of the support filler proximate the fitting proximal portion is greater than the density of the support filler proximate the fitting distal portion.

Aspect 25 can include, or can optionally be combined with the subject matter of Aspects 1-24 to optionally include wherein the at least one fitting material includes at least first and second fitting materials, and the first fitting material is proximate the fitting proximal portion and the second fitting material is proximate the fitting distal portion.

Aspect 26 can include, or can optionally be combined with the subject matter of Aspects 1-25 to optionally include a method of supporting a catheter comprising: deflecting a catheter shaft into a curved configuration; and supporting the catheter shaft in the curved configuration with a graduated strain relief fitting, supporting includes: bracing the catheter shaft at a hub interface between the catheter shaft and a hub with a fitting proximal portion of the graduated strain relief fitting, the fitting proximal portion having a first flexural modulus; and bracing the catheter shaft at a fitting interface distal to the hub interface with a fitting distal portion, the fitting distal portion having a second flexural modulus less than the first flexural modulus and less than or equal to a shaft flexural modulus of the catheter shaft.

Aspect 27 can include, or can optionally be combined with the subject matter of Aspects 1-26 to optionally include wherein supporting the catheter shaft in the curved configuration includes inhibiting kinking of the catheter shaft at each of the hub interface and the fitting interface according to the bracing at each of the hub and fitting interfaces.

Aspect 28 can include, or can optionally be combined with the subject matter of Aspects 1-27 to optionally include wherein supporting the catheter shaft includes bracing the catheter shaft between the hub and fitting interfaces with a graduated flexural modulus between the first and second flexural moduli.

Aspect 29 can include, or can optionally be combined with the subject matter of Aspects 1-28 to optionally include wherein bracing the catheter shaft between the hub and fitting interfaces includes continually decreasing the graduated flexural modulus from the first flexural modulus to the second flexural modulus.

Aspect 30 can include, or can optionally be combined with the subject matter of Aspects 1-29 to optionally include wherein supporting the catheter shaft includes controlling at least the first flexural modulus and the second flexural modulus with a scalloped profile including one or more scalloped flexure joints.

Aspect 31 can include, or can optionally be combined with the subject matter of Aspects 1-30 to optionally include wherein controlling at least the first and second flexural moduli includes increasing a joint pitch of the one or more scalloped flexure joints proximate to the fitting interface.

Aspect 32 can include, or can optionally be combined with the subject matter of Aspects 1-31 to optionally include wherein supporting the catheter shaft includes controlling at least the first flexural modulus and the second flexural modulus including controlling a wall thickness of a fitting body of the graduated strain relief fitting.

Aspect 33 can include, or can optionally be combined with the subject matter of Aspects 1-32 to optionally include wherein controlling the wall thickness of the fitting body includes tapering of the fitting body.

Aspect 34 can include, or can optionally be combined with the subject matter of Aspects 1-33 to optionally include wherein supporting the catheter shaft includes controlling at least the first flexural modulus and the second flexural modulus including controlling the fitting material of a fitting body of the graduated strain relief fitting.

Aspect 35 can include, or can optionally be combined with the subject matter of Aspects 1-34 to optionally include wherein controlling the fitting material includes having a first fitting material proximate the hub interface and having a second fitting material different from the first fitting material proximate the fitting interface.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A catheter assembly comprising:
   a catheter shaft extending between a shaft proximal portion and a shaft distal portion;
   a hub coupled with the catheter shaft proximate the shaft proximal portion, wherein the hub includes a hub profile larger than a shaft profile of the catheter shaft; and
   a graduated strain relief fitting coupled between the catheter shaft and the hub, the graduated strain relief fitting includes:
      one or more scalloped flexure joints between a fitting proximal portion and a fitting distal portion and extending over the catheter shaft, the one or more scalloped flexure joints having a modulating scalloped profile;
      a fitting frame between the one or more scalloped flexure joints, the fitting frame having a modulating frame profile;
      at least a first flexural modulus proximate the hub and the fitting proximal portion;
      at least a second flexural modulus proximate the catheter shaft and the fitting distal portion, the second flexural modulus is less than the first flexural modulus and less than or equal to a catheter shaft flexural modulus; and
      wherein the modulating scalloped profile increases in proportion to the modulating frame profile from the fitting proximal portion to the fitting distal portion and the modulating frame profile decreases in proportion to the modulating scalloped profile from the fitting proximal portion to the fitting distal portion.

2. The catheter assembly of claim 1, wherein a first wall thickness of the graduated strain relief fitting proximate the one or more scalloped flexure joints is less than a second wall thickness of the remainder of the graduated strain relief fitting.

3. The catheter assembly of claim 1, wherein the one or more scalloped flexure joints include one or more channels, grooves, flutes, helical grooves, notches, recesses, dimples or scoring.

4. The catheter assembly of claim 1, wherein a first joint pitch of the one or more scalloped flexure joints proximate the fitting proximal portion having the first flexural modulus is less than a second joint pitch at the fitting distal portion having the second flexural modulus.

5. The catheter assembly of claim 1, wherein the graduated strain relief fitting includes the fitting frame between the one or more scalloped flexure joints, and a first wall thickness proximate the fitting frame is greater than a second wall thickness proximate to the one or more scalloped flexure joints.

6. The catheter assembly of claim 5, wherein a first frame pitch of the fitting frame proximate to the fitting proximal portion is greater than a second frame pitch proximate to the fitting distal portion.

7. The catheter assembly of claim 1, wherein the graduated strain relief fitting includes at least one fitting material, and the fitting material proximate the fitting proximal portion provides the first flexural modulus, and the fitting material proximate the fitting distal portion provides the second flexural modulus.

8. The catheter assembly of claim 7, wherein the at least one fitting material includes a support filler, and the density of the support filler proximate the fitting proximal portion is greater than the density of the support filler proximate the fitting distal portion.

9. The catheter assembly of claim 7, wherein the at least one fitting material includes a graduated decreasing flexural modulus between the first flexural modulus proximate the fitting proximal portion and the second flexural modulus proximate the fitting distal portion.

10. The catheter assembly of claim 7, wherein the at least one fitting material includes at least first and second fitting materials, and the first fitting material is proximate the fitting proximal portion and the second fitting material is proximate the fitting distal portion.

11. The catheter assembly of claim 1, wherein the graduated strain relief fitting includes a strain relief profile between the fitting proximal and distal portions, the strain relief profile includes each of the modulating frame profile and the modulating scalloped profile;
the modulating frame profile has a greater proportion of the strain relief profile proximate to the fitting proximal portion relative to the modulating scalloped profile; and
the modulating scalloped profile has a greater proportion of the strain relief profile proximate to the fitting distal portion relative to the modulating frame profile.

12. The catheter assembly of claim 1, wherein the modulating scalloped profile increases from the fitting proximal portion to the fitting distal portion and the modulating frame profile conversely decreases from the fitting proximal portion to the fitting distal portion.

13. The catheter assembly of claim 1, wherein the one or more scalloped flexure joints proximate the fitting distal portion are a larger proportion of the fitting distal portion relative to the fitting proximal portion, and the one or more scalloped flexure joints proximate the fitting proximal portion are a smaller proportion of the fitting proximal portion relative to the fitting distal portion.

14. A method of supporting a catheter comprising:
deflecting a catheter shaft into a curved configuration; and
supporting the catheter shaft in the curved configuration with a graduated strain relief fitting, supporting includes:
bracing the catheter shaft at a hub interface between the catheter shaft and a hub with a fitting proximal portion of the graduated strain relief fitting, the fitting proximal portion having a first flexural modulus;
bracing the catheter shaft at a fitting interface distal to the hub interface with a fitting distal portion, the fitting distal portion having a second flexural modulus less than the first flexural modulus and less than or equal to a shaft flexural modulus of the catheter shaft; and
wherein the first and second flexural moduli are based on scalloped flexure joints having a modulating scalloped profile, the scalloped flexure joints extend over the catheter shaft, and a fitting frame having a modulating frame profile the fitting frame between the scalloped flexure joints:
the modulating scalloped profile increases in proportion to the modulating frame profile from the fitting proximal portion to the fitting distal portion; and
the modulating frame profile decreases in proportion to the modulating scalloped profile from the fitting proximal portion to the fitting distal portion.

15. The method of claim 14, wherein supporting the catheter shaft in the curved configuration includes inhibiting kinking of the catheter shaft at each of the hub interface and the fitting interface according to the bracing at each of the hub and fitting interfaces.

16. The method of claim 14, wherein supporting the catheter shaft includes bracing the catheter shaft between the hub and fitting interfaces with a graduated flexural modulus between the first and second flexural moduli.

17. The method of claim 16, wherein bracing the catheter shaft between the hub and fitting interfaces includes continually decreasing the graduated flexural modulus from the first flexural modulus to the second flexural modulus.

18. The method of claim 14, wherein controlling at least the first and second flexural moduli includes increasing a joint pitch of the one or more scalloped flexure joints proximate to the fitting interface.

19. The method of claim 14, wherein supporting the catheter shaft includes controlling at least the first flexural modulus and the second flexural modulus including controlling a wall thickness of a fitting body of the graduated strain relief fitting.

20. The method of claim 19, wherein controlling the wall thickness of the fitting body includes tapering of the fitting body.

21. The method of claim 14, wherein supporting the catheter shaft includes controlling at least the first flexural modulus and the second flexural modulus including controlling the fitting material of a fitting body of the graduated strain relief fitting.

22. The method of claim 21, wherein controlling the fitting material includes having a first fitting material proximate the hub interface and having a second fitting material different from the first fitting material proximate the fitting interface.

* * * * *